United States Patent [19]

Warkentin

[11] Patent Number: 5,459,322

[45] Date of Patent: Oct. 17, 1995

[54] ULTRAVIOLET LIGHT CHAMBER

[75] Inventor: Kenneth Warkentin, Collegeville, Pa.

[73] Assignee: Therakos, Inc., Westchester, Pa.

[21] Appl. No.: 166,403

[22] Filed: Dec. 14, 1993

[51] Int. Cl.$^6$ .............................. G01N 23/00; H01J 37/20
[52] U.S. Cl. ........................................................ 250/455.11
[58] Field of Search ......................... 250/454.11, 455.11

[56] References Cited

U.S. PATENT DOCUMENTS

| | | | |
|---|---|---|---|
| 2,146,688 | 2/1939 | Selig | 250/455.11 |
| 2,253,250 | 8/1941 | Selig | 250/455.11 |
| 3,433,949 | 3/1969 | Truhan | 250/455.11 |
| 4,708,715 | 11/1987 | Troutner | 604/6 |
| 4,726,949 | 2/1988 | Miripol et al. | 424/101 |
| 4,727,027 | 2/1988 | Wiesehahn et al. | 435/173 |
| 4,866,282 | 9/1989 | Miripol et al. | 250/455.11 |
| 4,952,812 | 8/1990 | Miripol et al. | 250/455.1 |

Primary Examiner—Bruce C. Anderson

[57] ABSTRACT

Methods and apparatus for exposing a sample to ultraviolet radiation are disclosed. The present invention permits a sample contained within a shielded housing to be exposed to a source of ultraviolet radiation and simultaneously observed. The sample rests on a stage that can be moved relative to the source of the ultraviolet radiation while the irradiation is taking place, thus the effects of ultraviolet radiation upon biological materials such as blood can be determined. In a preferred embodiment, upper and lower banks of ultraviolet bulbs are disposed on either side of the stage. The movement of the banks of bulbs and the stage relative to one another is preferably controlled by a set of lead screws. In certain embodiments, the intensity of the emissions of the bulbs themselves can also be altered while continuously observing and irradiating the sample. The invention preferably uses radiation at a wavelength in the UV-B band, between about 280–320 nm or, more preferably, in the UV-A band, between about 320–400 nm.2

4 Claims, 1 Drawing Sheet

ULTRAVIOLET LIGHT CHAMBER

The present invention relates to methods and apparatus for exposing materials to a source of electromagnetic radiation. More particularly, the present invention relates to the controlled exposure of samples of biological materials such as blood to ultraviolet light.

Background of the Invention

Certain effects caused by irradiating blood products with ultraviolet light are known. For example, U.S. Pat. No. 4,726,949—Miripol, et al. discloses methods whereby a thin film of white blood cells are irradiated with ultraviolet radiation within the UV-B band at a wavelength of 280–320 nanometers (nm). Such irradiation causes the white blood cells to lose their capability to set off an immune reaction in an alloimmunized patient. As disclosed in the above-mentioned patent, and in related U.S. Pat. No. 4,726,949 also to Miripol, et al., the blood cells should be in a thin film that is inserted between two banks of UV-B bulbs mounted a fixed distance apart within a cabinet. Because the intensity of the UV-B radiation and the geometry of the emitters are fixed, the effect of the ultraviolet radiation is described as a function of total energy exposure per unit area.

U.S. Pat. No. 4,727,027—Wieshahn et al. discloses decontaminating blood and blood components by treating the blood with furocoumarin derivatives followed by irradiation with UV-A radiation having a wavelength between about 300–400 nm at an intensity between 0.1 mW/cm and 5.0 w/cm. No apparatus is disclosed for carrying out this technique.

In general, the qualitative and quantitative effects of ultraviolet radiation upon many biological materials remains largely undetermined. In particular, the effects of ultraviolet radiation in the UV-A band (320–400 nm) upon biological materials is being actively investigated. As used herein, the term "biological materials" is meant to encompass blood and components of blood, as well as any other fluid produced by or present within a living organism, alone or mixed with another substance, such as a photodynamic reagent. Presently, it would be desirable for researchers to be able to vary degree of exposure to which a particular sample of biological material is subjected. As used herein, the term "degree of exposure" includes a both the intensity of the emission, e.g., the power level and the distance between the source of ultraviolet radiation and the sample, as well as other factors such as the time of exposure.

Currently available ultraviolet sources have a narrow range of intensity. Moreover, ultraviolet sources found in the prior art are in the form of individually mounted bulbs that require time consuming bulb changing operations, caused by various bulbs in a bank failing at different times. When one of a bank of bulbs burns out, the uniformity of the degree of exposure to the ultraviolet radiation is altered, and even when replaced, there may be bulb-to-bulb variations in intensity since the bulbs have burned for differing amounts of time. Finally, changing individual bulbs increases the possibility of damaging the sockets into which the bulbs are inserted.

Ideally, parameters such as intensity should be altered on a continuous basis so that the effect upon a sample or group of samples could be observed. However, repeated exposure to ultraviolet radiation poses a health hazard to the worker. Although some hazards can be mitigated by protective measures such as eyewear that blocks ultraviolet rays, such measures usually interfere with the observation of the samples. Thus, if an alteration or adjustment of the samples or equipment requires opening a shielded enclosure or otherwise entering the area upon which the ultraviolet radiation impinges the emissions must be discontinued, thereby interrupting the investigation. Thus, it would be desirable to adjust intensity externally to permit an experiment to run continuously. It is therefore an object of the present invention to provide methods and apparatus whereby the degree of exposure to ultraviolet radiation to which a sample is subjected can be continuously and safely varied while an ultraviolet radiation emitter is activated.

Additionally, it would be desirable to provide an apparatus that would support a sample in an accurately predetermined location without blocking the incident ultraviolet radiation. It would also be desirable to prevent excessive heat build-up within the enclosure containing the samples, since it is known that exposure to elevated temperatures can have a deleterious effect upon biological materials. It is therefore a further object of the present invention to provide methods and apparatus for exposing a sample to ultraviolet radiation that permit both accurate and repeatable positioning of samples relative to a source of ultraviolet radiation and reduce the build-up of heat.

SUMMARY OF THE INVENTION

It has now been found that these and other objects can be obtained using apparatus for irradiating a container having a sample of biological materials therein with ultraviolet radiation that includes a housing and a upper and lower sources of ultraviolet radiation disposed within the housing. The upper source of ultraviolet radiation is located above the first source and is moveable relative to the lower source, and a stage for retaining the container is provided that is disposed between the lower and upper sources. The distance between the lower source and the stage is also adjustable and is accomplished by moving the stage relative to the lower source. In preferred embodiments, a lead screw is connected to the upper source for moving the upper source relative to the lower source, and a lead screw is also connected to either the lower source or the stage to effect its motion. The sources of ultraviolet radiation used in the present invention preferably either emit radiation at a wavelength in the UV-B band, between about 280–320 nm or, more preferably, in the UV-A band, between about 320–400 nm. Also, in certain preferred embodiments, the upper and lower source is a cassette comprised of a bank of aligned ultraviolet lamps.

The present invention also discloses methods of irradiating a sample with ultraviolet radiation, as well as improved methods of treating blood components with ultraviolet radiation. The methods of the present invention take advantage of ability to change the distance between a sample and a source of ultraviolet radiation while continuously irradiating and observing the sample. This feature, sometimes used in conjunction with changing the intensity of the ultraviolet emissions, permits the effects of ultraviolet radiation upon samples of biological materials such as blood to be determined.

DETAILED DESCRIPTION OF THE PREFERRED EMBODIMENTS

The present invention solves the problems found in prior art irradiation apparatus and permits the action of ultraviolet radiation on biological materials to be safely investigated. As explained in further detail below, the safety enhancing aspects of the present invention preferably include a combination of shielding, a door interlock switch, and the provision of external controls that adjust the intensity and the position of two sources of ultraviolet radiation relative to a platform upon which one or more samples of biological material rest. One advantage of the system disclosed is that the degree of exposure can be continuously changed while safely observing the effect of the ultraviolet radiation on the sample.

Figure 1:
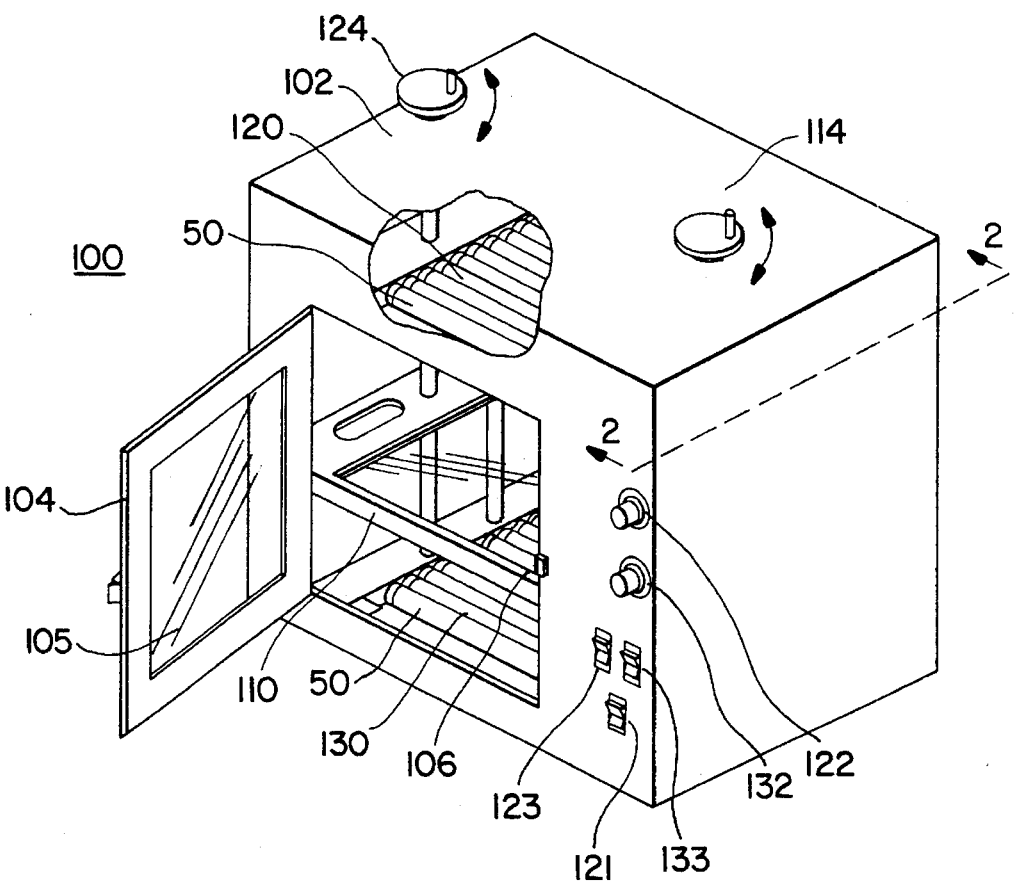
FIG. 1 is a perspective view, partially cut away, of an ultraviolet light box constructed in accordance with the present invention.

As illustrated in a perspective view in FIG. 1, a light box 100 in which lamp intensity is continuously variable over a wide range in accordance with the present invention is shown. The light box 100 includes a shielded housing 102 that contains the various components described below. The housing 102 may be constructed of any suitable material that will contain ultraviolet radiation safely and withstand the operating temperatures of the system when in operation. In the preferred embodiment illustrated in FIG. 1, a stage 110 for samples (not illustrated) is disposed between an upper lamp bank 120, visible in the broken away portion of FIG. 1, and a lower lamp bank 130. The stage preferably has a central section 112 comprised of a material that is transparent to ultraviolet radiation to permit radiation emanating from the lamp banks 120,130 to impinge upon either side of a sample or group of samples. It should be understood that the samples themselves are contained within containers that are transparent to at least certain wavelengths of ultraviolet radiation. In the embodiment illustrated, the stage 110 preferably has dimensions of about 12×14 inches to permit nearly any typical size sample or group of samples to be accepted. The maximum distance (height) between the upper lamp bank 120 and the lower lamp bank 130 is about preferably 14½ inches.

In accordance with the present invention, the lamp banks 120,130 can be individually switched and controlled in intensity. Typically, intensity control is provided by control knobs 122,132 that are connected to a potentiometer or other device that individually varies the voltage supplied to the lamp banks 120,130, thereby varying the intensity of the ultraviolet emissions. Because the control knobs 122,132 are placed on the exterior surface of the housing 102, the intensity can be safely adjusted while the unit is in operation. Also shown in FIG. 1 are power switches 123,133 that control the power to the lamp banks 120,130 and the main power switch 121.

Figure 2:
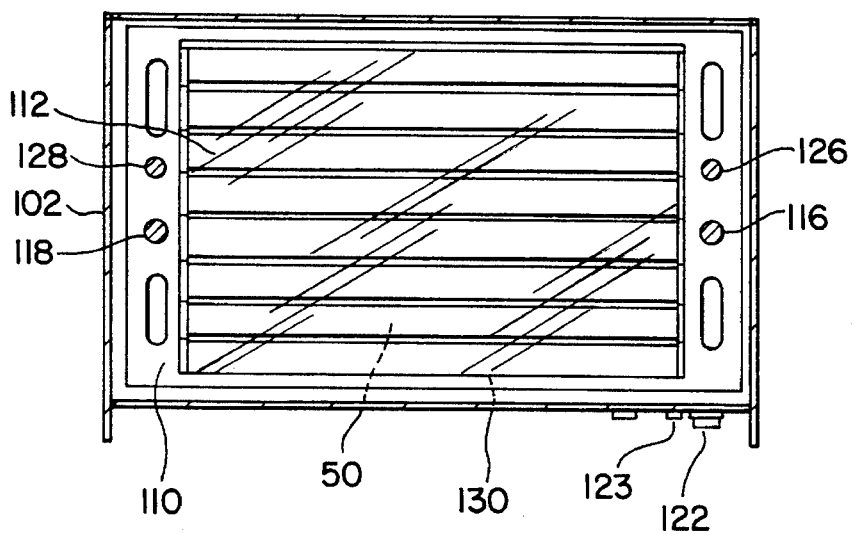
FIG. 2 is a cross-sectional top plan view, taken along line 2—2 of the apparatus illustrated in FIG. 1.

Another aspect of the present invention involves the adjustability of the relative distances between the stage 110 and the lamp banks 120,130. Referring still to FIG. 1, it can be seen that an upper bank adjustment knob 124 and a stage adjustment knob 114 are provided to adjust these distances. A cross-sectional top plan view of the apparatus illustrated in FIG. 1 is shown in FIG. 2, with the top surface of the housing 102 and the upper bank 120 removed to illustrate this aspect of the invention. In the preferred embodiment illustrated in FIGS. 1–2, the adjustment knobs 114,124 are connected, respectively, to lead screws 116,118 and 126,128. Each pair of lead screws 116,118 and 126,128 is preferably connected so that the rotation of the associated adjustment knob is transferred equally to each screw. As a result, the movement of either the upper lamp bank 120 or the stage 110 is maintained parallel and precise relative to the rest of the assembly.

Still referring to FIGS. 1–2, the lamps banks 120,130 are preferably moveable to within one inch of the stage 110. Thus, in the preferred embodiment illustrated, wherein the lower bank of lamps is fixed, the stage 110 and upper lamp bank 120 are individually adjustable in height whereby the stage 110 can be positioned at any height up to within one inch of either lamp bank 120,130, and the upper lamp bank 120 is brought down within about two inches of the lower lamp bank 130.

Although connected pairs of lead screws are employed in preferred embodiments of the present invention, those of skill in the art will realize that other mechanical and electromechanical apparatus may be employed to move either or both of the upper lamp bank 120 or the stage 110 relative to one another and the lower lamp bank 130 while maintaining the surfaces of each of these portions of the assembly parallel. For example, linear gear tracks could be used in place of the lead screws and mesh with properly positioned sets of gears connected to the lamp banks and stage. The components are then moved by driving one or more of the gears, either manually or with a motor. Another example of an alternative embodiment is to connect sets of pulleys affixed to the lamp banks and stage to driving mechanisms and each other using cables. By choosing appropriate idler pulleys and cable arrangements, the movement of the lamp banks and stage would remain parallel and could again be effected using either adjustment knobs or a motor to take up the ends of the cables. Finally, in any embodiment, the position of the lamp banks and stage can be sensed and controlled, either for absolute position relative to the housing or for position relative to each other.

Although it is preferred that the lower lamp bank 130 remain fixed, it will be realized that in certain embodiments it will be further desirable to add a set of lead screws or equivalent structure to the lower lamp bank 130 to permit it to be adjusted relative to the stage 110 as well. In such embodiments, it may be desirable to have the stage remain in a fixed position and vary the distance between the stage 110 and the upper lamp bank 120 in the manner described above, while varying the distance between the lower lamp bank 130 and the stage 110 in a manner similar to that described above with relation to the mechanism whereby the position of the stage 110 was moved.

Using the above-described combination of adjusting the intensity of the lamp banks 120,130 and adjusting the relative distances between the stage 110 and the lamp banks 120,130, the present invention provides a continuous and wide range variability of lamp intensity by external control.

The system of the present invention is enclosed and interlocked for operator safety. The lamp banks 120,130 can be positioned with respect to the stage 110 without opening the safety enclosure. As shown in FIG. 1, large UV-blocking window 105 is preferably provided in the door 104 of the housing 102. The window 105 is most preferably comprised of transparent polycarbonate to provide a safe and complete view of the chamber within the interior of the housing 102 and the stage 110. Also visible in FIG. 1 is an interlock switch 106 that prevents activating the ultraviolet light banks 120,130 when the door 104 is open.

As shown in both FIGS. 1–2, the lamp banks 120,130 are preferably comprised of a plurality of tubular ultraviolet bulbs 50. The bulbs 50 are most preferably mounted in a disposable cassette, ensuring that all bulbs have the same life and the same time of operation. The chances of socket damage from replacing individual bulbs is thus eliminated. Thus, at or near the end of the life of the bulbs 50, the entire cassette assembly is simply replaced. This arrangement provides more reliable operation, reduces the likelihood of socket damage and minimizes the amount of time that the light box 100 is not available for use.

Enclosing two banks of ultraviolet light tubes in a closed environment will result in the build up of heat within the enclosed space. Thus, in preferred embodiments o f the present invention, heat build-up is controlled by forced draft ventilation with baffled air flow to ensure adequate cooling of the chamber. As known to those of skill in the art, one or more small fans can be disposed at any convenient location within the enclosure to either force ambient air into the enclosure, expel hot air from the enclosure, or both.

The present invention therefore discloses methods of irradiating a sample with ultraviolet radiation by placing the sample on a stage within a shielded housing, and then moving the stage and a lower source of ultraviolet radiation relative to one another and moving an upper source of ultraviolet radiation relative to the stage. The upper and lower sources are then activated. Preferably, as described above, the step of moving the stage and the upper and lower sources comprises rotating a lead screw.

In general, the methods disclosed herein are useful, for example, to treat blood components with ultraviolet radiation. In use, the blood components are placed in a sample container that is placed in a chamber at a first distance from a source of ultraviolet light. The sample container is irradiated and observed during irradiation. In accordance with the present invention, it is now possible for the sample to be moved to a location that is a second distance from the source of ultraviolet light while continuing to irradiate and observe the sample. Additionally, as explained above, the initial intensity of the ultraviolet source can also be varied while continuously irradiating and observing the sample. In this manner the present invention permits the effects of ultraviolet radiation upon the sample to be determined.

Although certain preferred embodiments of the present invention have been described herein with detail, these examples are meant to illustrate the present invention and are not limiting. Upon review of the foregoing descriptions in conjunction with the drawings, those of skill in the art will realize that a number of adaptations, variations and modifications that depart from the precise embodiments disclosed are possible. However, such alternate embodiments will nonetheless utilize the present invention. Accordingly, reference should be made to the appended claims in order to determine the full scope of the present invention.

What is claimed:

1. Apparatus for irradiating with ultraviolet radiation a container having a sample of biological materials therein, said apparatus comprising:

a housing;

a lower source of ultraviolet radiation disposed within the housing;

an upper source of ultraviolet radiation disposed within the housing above the lower source, said upper source being connected to a lead screw for moving the upper source relative to the lower source; and a stage for retaining the container disposed within the housing between the upper source and the lower source, said stage being connected to a lead screw for moving the stage relative to the lower source.

2. The apparatus of claim 1, wherein the lower and upper sources of ultraviolet radiation emit radiation at a wavelength in the UV-A band, between about 320–400 nm.

3. The apparatus of claim 1, wherein the lower and upper sources of ultraviolet radiation emit radiation at a wavelength in the UV-B band, between about 280–320 nm.

4. The apparatus of claim 1 wherein at least one of the upper source and the lower source is a cassette comprised of a bank of aligned ultraviolet lamps.

* * * * *